US008451442B2

(12) United States Patent
Benderskii et al.

(10) Patent No.: US 8,451,442 B2
(45) Date of Patent: May 28, 2013

(54) ENHANCED SURFACE-SELECTIVE SPECTROSCOPY USING BROAD-BAND HETERODYNE-DETECTED SUM FREQUENCY GENERATION

(75) Inventors: Alexander V. Benderskii, La Canada Flintridge, CA (US); Igor V. Stiopkin, Madison, WI (US); Himali Dilrukshi Jayathilake, South Hadley, MA (US)

(73) Assignee: Wayne State University, Detroit, MI (US)

( * ) Notice: Subject to any disclaimer, the term of this patent is extended or adjusted under 35 U.S.C. 154(b) by 407 days.

(21) Appl. No.: 12/452,192

(22) PCT Filed: Jun. 18, 2008

(86) PCT No.: PCT/US2008/007579
§ 371 (c)(1),
(2), (4) Date: Jun. 23, 2010

(87) PCT Pub. No.: WO2008/156776
PCT Pub. Date: Dec. 24, 2008

(65) Prior Publication Data
US 2010/0265501 A1    Oct. 21, 2010

Related U.S. Application Data

(60) Provisional application No. 60/936,242, filed on Jun. 18, 2007.

(51) Int. Cl.
*G01J 3/28*    (2006.01)

(52) U.S. Cl.
USPC ............................................................. 356/326

(58) Field of Classification Search
USPC ............................................................. 356/326
See application file for complete search history.

(56) References Cited

U.S. PATENT DOCUMENTS

| 6,081,332 | A   | * | 6/2000 | Kojima ......................... 356/334 |
| 6,611,336 | B1  | * | 8/2003 | Walmsley et al. ............ 356/450 |
| 6,744,518 | B2  | * | 6/2004 | Dress et al. .................. 356/450 |
| 7,075,660 | B2  | * | 7/2006 | Farmiga et al. ............... 356/511 |
| 7,333,212 | B2  | * | 2/2008 | Chou et al. .................... 356/484 |

* cited by examiner

*Primary Examiner* — Tu Nguyen
(74) *Attorney, Agent, or Firm* — Rohm & Monsanto, PLC (57) ABSTRACT

Method and apparatus for performing spectroscopy, include the combining of first and second light beams to form a reference beam, focusing the first and second light beams and the reference beam onto a sample, receiving a reflected light beam from the sample at a monochromator, and viewing a predetermined wavelength band of the reflected light beam from the monochromator. Portions of the first and second light beams, which may be visible and IR forms of electromagnetic energy, are heterodyned through a crystal. A monochromator receives a reflection of the reference beam from the sample, and Fourier transformation is performed on the output of the monochromator. The first and second beams of electromagnetic energy can be split to form first and second component beams and the reference beam, all of which are propagated to the sample.

20 Claims, 8 Drawing Sheets

ENHANCED SURFACE-SELECTIVE SPECTROSCOPY USING BROAD-BAND HETERODYNE-DETECTED SUM FREQUENCY GENERATION

RELATIONSHIP TO OTHER APPLICATION

This application is a US national stage filing under 35 U.S.C. §371 of International Application Serial Number PCT/US2008/007579 filed on Jun. 18, 2008 and claims the benefit of the filing date of U.S. Provisional Patent Application Ser. No. Ser. No. 60/936,242, filed Jun. 18, 2007, Conf. No. 3441 (Foreign Filing License Granted) in the names of the same inventors as herein. The disclosure in the identified United States Provisional Patent Application is incorporated herein by reference.

GOVERNMENT RIGHTS

This invention was made under contract awarded by the NSF, Career Grant No. CHE-0449720. The government has certain rights in the invention.

BACKGROUND OF THE INVENTION

1. Field of the Invention

This invention relates generally to spectroscopy, and more particularly, to a broad-band heterodyne-detected sum frequency generation (HD-SFG) spectroscopy having high sensitivity to enable surface-selective measurements of vibrational spectra at sub-monolayers surface coverage.

2. Description of the Prior Art

Detection of adsorbed molecules at interfaces is of paramount importance in many areas of chemistry, physics, and biology, ranging from surface functionalization chemistry, electrochemistry, and heterogeneous catalysis, to semiconductor passivation, biofouling, and cell membrane biology. In the past decade, vibrational sum frequency generation (SFG) spectroscopy has emerged as one of the main tools for characterization of the molecular structure and dynamics at interfaces. Its advantages are (1) the richness of the molecular-level information (e.g., orientation and conformation) available from the fingerprint mid-IR spectra and (2) the surface selectivity that allows monolayer sensitivity without introducing fluorescent labels or resorting to surface enhancement techniques which typically require a metal surface.

However, improving the detection limits of SFG below a single monolayer coverage has proven to be a challenge. The main reason is that in its conventional homodyne-detected implementation, the intensity of the coherent second-order nonlinear SFG signal scales unfavorably (quadratically) with the surface coverage N of the analyte molecules:

$$I_{SFG} \propto |E_{SFG}|^2 \propto |x^{(2)}|^2 = N^2 |\langle \beta^2 \rangle|^2 \quad (1)$$

where $x^2 = N \langle \beta^{(2)} \rangle$ is macroscopic nonlinear susceptibility of the surface expressed through the molecular hyperpolarizability $\beta^{(2)}$ averaged over the orientational distribution at the interface. This implies that detection of 10% of a monolayer entails a factor of 100 decrease in the SFG signal intensity compared to a close-packed monolayer, essentially prohibiting vibrational SFG spectroscopy of samples significantly below monolayer coverage (note, in order to gain a factor of 100 in the signal-to-noise ratio, $\times 10^4$ longer acquisition would be required at the same laser intensity).

Optical heterodyne detection has been demonstrated to enhance sensitivity of many coherent spectroscopies for bulk-phase studies.

There is a need, therefore, for a heterodyne-detected HD-SFG spectroscopy which overcomes the limitations of the conventional (homodyne-detected) SFG technique.

SUMMARY OF THE INVENTION

The invention herein disclosed is a new technique of heterodyne-detected SFG spectroscopy that is characterized by high sensitivity so as to enable measurements of vibrational spectra of sub-monolayers, at surface coverage as low as a few % of a monolayer. In accordance with the invention, this is achieved on a transparent dielectric substrate, such as water, without resorting to the total internal reflection geometry, and without the help of surface enhancement phenomena. In contrast to the ultrasensitive fluorescence detection, which requires utilization of electronic transitions and/or introduction of fluorescent labels, only the intrinsic vibrational resonances are employed in the detection of the analyte (1-octanol) molecules. Octanol is a straight chain fatty alcohol with eight carbon atoms and the molecular formula $CH_3(CH_2)_7OH$. The term "octanol" usually refers exclusively to the primary alcohol 1-octanol.

In accordance with a first method of performing spectroscopy according to the invention, there are provided the steps of combining first and second light beams to form a reference beam, focusing the first and second light beams and the reference beam onto a sample desired to be investigated, receiving a reflected light beam from the sample at an input of a monochromator, and viewing a predetermined wavelength band of the reflected light beam at an output of the monochromator.

In one embodiment of this method aspect of the invention, the step of combining includes the step of propagating a portion of the first light beam and a portion of the second light beam through a crystal. Difference frequency mixing, or heterodyning, is effected in this manner.

The first light beam is, in one embodiment, an IR light, the second light beam is a visible light, and the crystal is formed of $KNbO_3$. In other embodiments, the crystal is a $AgGaS2$ crystal.

The step of viewing includes in some embodiment of the invention the further step of propagating the predetermined wavelength band of the reflected light beam from the output of the monochromator to a camera. The predetermined wavelength band of the reflected light beam is then subjected to inverse Fourier transformation to produce a corresponding time-domain representation of the predetermined wavelength band of the reflected light beam. Subsequently, the time-domain representation of the predetermined wavelength band of the reflected light beam is subjected to fast Fourier transform (FFT) and the real part of the resulting frequency domain representation is extracted. Then, the absolute value of the real part of the resulting frequency domain representation is determined in some embodiments.

An optical delay stage is, in some embodiment, interposed in the path of a selected one of the first and second light beams.

In accordance with an apparatus aspect of the invention, there is provided s spectroscopy system having first and second inputs for receiving respective ones of first and second beams of electromagnetic energy. A beam splitter divides the first beam of electromagnetic energy into first and second sub-beams of electromagnetic energy. A crystal propagates the first sub-beam of electromagnetic energy of the first beam of electromagnetic energy and the second beam of electromagnetic energy simultaneously, to produce a combined reference beam of electromagnetic energy. Then, a reflector element directs the reference beam toward a sample that is desired to be investigated. In some embodiments, the reflector element additionally direct the second beam of electromagnetic energy and the second sub-beam of electromagnetic energy of the first beam of electromagnetic energy toward the sample that is desired to be investigated.

The crystal enables the heterodyning of the beams of electromagnetic energy to produce the reference beam that has a frequency that is responsive to the heterodyning effect.

A monochromator receives a reflection of the reference beam from the sample under investigation. Then, an analysis system conducts, in some embodiments of the invention, a Fourier transformation is performed on the output of the monochromator.

In one embodiment of the invention, the crystal if formed of $AgGaS_2$ crystal. In other embodiments, the crystal is a $KNbO_3$ crystal.

In accordance with a further method aspect of the invention, there is provided a method of performing spectroscopy, the method having the steps of splitting each of first and second beams of electromagnetic energy to form respectively associated first and second component beams for each of the first and second beams of electromagnetic energy and combining the first component beams of each of the first and second light beams in a crystal to form a reference beam. In addition, the reference beam is focused onto a sample desired to be investigated.

In one embodiment of this further method aspect the invention, the step of focusing the reference beam onto a sample desired to be investigated includes the further step of focusing the second component beams of each of the first and second light beams onto the sample desired to be investigated. The electromagnetic energy reflected from the sample is received at an input of a monochromator. The electromagnetic energy is then energy reflected from the sample toward at an input of a monochromator. However, in some embodiments, there is provided the further step of collimating the electromagnetic energy that is reflected from the sample.

The technique of the present invention find applications in ultrasensitive spectroscopic detection of molecules at surfaces/interfaces in chemistry and biology. The improved sensitivity will broaden the range of applications of the nonlinear surface-selective vibrational spectroscopy, in particular to the biological systems, e.g., probing surfaces of biomembranes.

The arrangement of the present invention is useful for probing molecular structure and dynamics at surfaces and interfaces. Second order nonlinear optical spectroscopy employs UV-vis, which is electronic Second Harmonic Generation (SHG); and IR, which is vibrational SFG (Sum Frequency Generation).

In accordance with the invention, there is provided a system of heterodyne-detected HD-SFG spectroscopy that linearizes the spectroscopic signal using interference of the SFG signal optical field $E_{SFG}$ with a reference beam, referred to as the "Local Oscillator" (LO), $E_{LO}$. In accordance with the invention, the total signal intensity in the heterodyne-detection scheme is:

$$I_{HD-SGG} \propto |E_{SFG} + E_{LO}|^2 = |E_{SFG}|^2 + |E_{LO}|^2 + 2\,\mathrm{Re}[E_{SFG}E^*_{LO}] \qquad (2)$$

By using the LO beam that is much stronger than the SFG signal, i.e., $E_{LO} \gg E_{SFG}$, the intensity of the cross term (last term in Eq. 2) is greatly enhanced, and after subtracting the independently measured LO intensity (second term), the extracted heterodyne signal (the so-called "Spectral Interferogram," hereinafter "SI") is linear in the SFG field, i.e. in the surface coverage:

$$I_{SI} \propto 2\,\mathrm{Re}[E_{SFG}E^*_{LO}] \propto N \langle \beta^{(2)} \rangle \qquad (3)$$

In this manner, heterodyne-detected sum frequency generation HD-SFG enables significant improvement of the signal-to-noise ratio by amplifying the weak SFG signal through interference with the strong LO reference beam. This allows one to obtain vibrational spectra at a few % monolayer coverage. In addition, heterodyne detection yields both amplitude and phase of the signal. This not only provides additional information about the molecular structure of the interface, but also allows correct subtraction of the background signal of the neat interface (the nonresonant electronic contribution as well as vibrations of impurities), a ubiquitous problem in situations when one is interested in detecting a low concentration of analyte molecules at a surface or interface, i.e. samples with weak resonant signal.

BRIEF DESCRIPTION OF THE DRAWING

Comprehension of the invention is facilitated by reading the following detailed description, in conjunction with the annexed drawing, in which.

DETAILED DESCRIPTION

Structure

Figure 1:
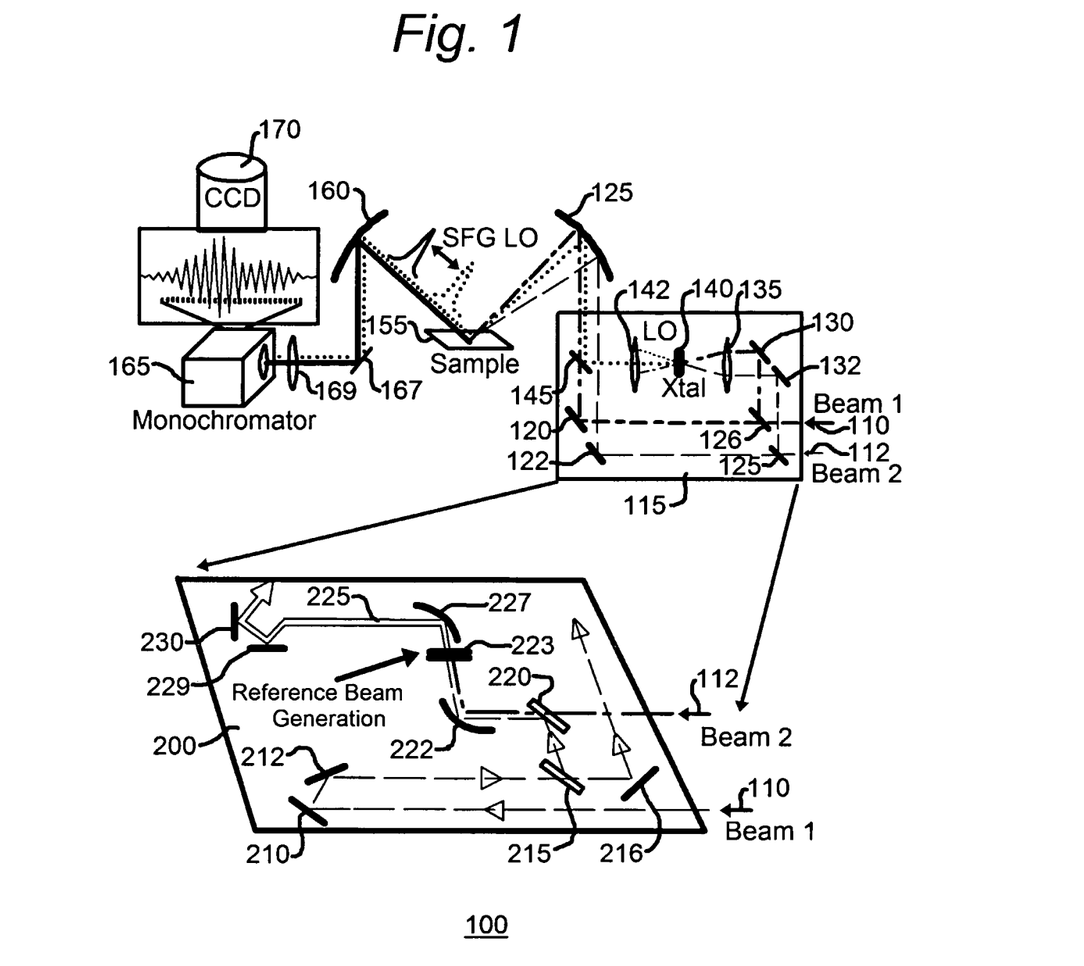
FIG. 1 is a simplified schematic representation of a spectroscopic apparatus constructed in accordance with the invention.

FIG. 1 is a simplified schematic representation of a spectroscopic apparatus 100 constructed in accordance with the invention. As shown in this figure, a first light beam 110 and 112 are propagated to an optical circuit 115. The light beams are propagated to respective mirrors 120 and 122 whereupon the beams are reflected to a concave reflector 125. Prior to reaching mirrors 120 and 122, the light beams are split by respective ones of beam splitters 126 and 128 and respective portions of the light beams are redirected to respective mirrors 130 and 132. Upon being reflected by mirrors 130 and 132, the light beams are focused by a lens 135 onto a crystal 140, and then focused again by a further lens 142. The refocused light beam constitutes a reference beam that is propagated in this embodiment toward a mirror 145 and onto concave reflector 125.

Concave reflector 125 focuses first beam 110, second beam 112, and reference beam 150 onto a sample 155. The combined beams are reflected from the sample onto a further concave reflector 160 and into a monochromator 165 via a further mirror 167 and a further lens 169. Monochromator 165 issues an optical signal (not specifically designated) that is viewed, in this specific illustrative embodiment of the invention, by charge coupled device (CCD) camera 170. As is known, a monochromator is an optical device that transmits a mechanically selectable narrow band of wavelengths of light from a wider range of wavelengths available at the input.

FIG. 1 shows a further arrangement 200 for generating a reference beam. Reference beam generating arrangement 200 is particularly advantageous as a retrofit for existing spectroscopic equipment. In the embodiment of reference beam generating arrangement 200, first and second light beams 110 and 112 are propagated to reference beam generating arrangement 200. First beam 110 is reflected as shown by mirrors 210 and 212 and propagated through a beam splitter 215. The portion of first beam 110 that propagates through beam splitter 215 is reflected by a further mirror 216.

Second light beam 112 is propagated through a beam splitter 220, which also reflects a portion of first light beam 110. The 3 second light beam and the portion of first light beam 110 that was split at beam splitter 215 are propagated to a concave reflector 222 and to a crystal 223. Crystal 223 issues the reference beam (225), which is reflected, in this specific illustrative embodiment of the invention, by reflector 227 and mirrors 229 and 230.

The broad-band vibrational sum frequency generation (SFG) spectroscopy arrangement described herein is based on a high power amplified femtosecond Ti-Sapphire laser system (Spectra Physics Spitfire sub-50 fs HP) (not shown). Fifty percent (50%) of the 2 mJ fundamental output pulse (800 nm, FWHM 35 fs) is used to pump an Optical Parametric Amplifier (OPA) followed by the signal-idler re-timing with a manual delay stage and difference frequency mixing in a 0.5 mm thick $AgGaS_2$ crystal producing 4-5 μJ IR pulses centered at 2900 $cm^{-1}$. The broad-band SFG scheme is employed that uses spectrally broad (FWHM~250 $cm^{-1}$) IR and narrow-band visible pulses obtained using a high-power deposited etalon (TecOptics), FWHM 15 $cm^{-1}$. The laser power at the sample 155 is 2-3 μJ/pulse for IR and up to 10-15 μJ/pulse for the visible at 1 kHz repetition rate.

Figure 2:
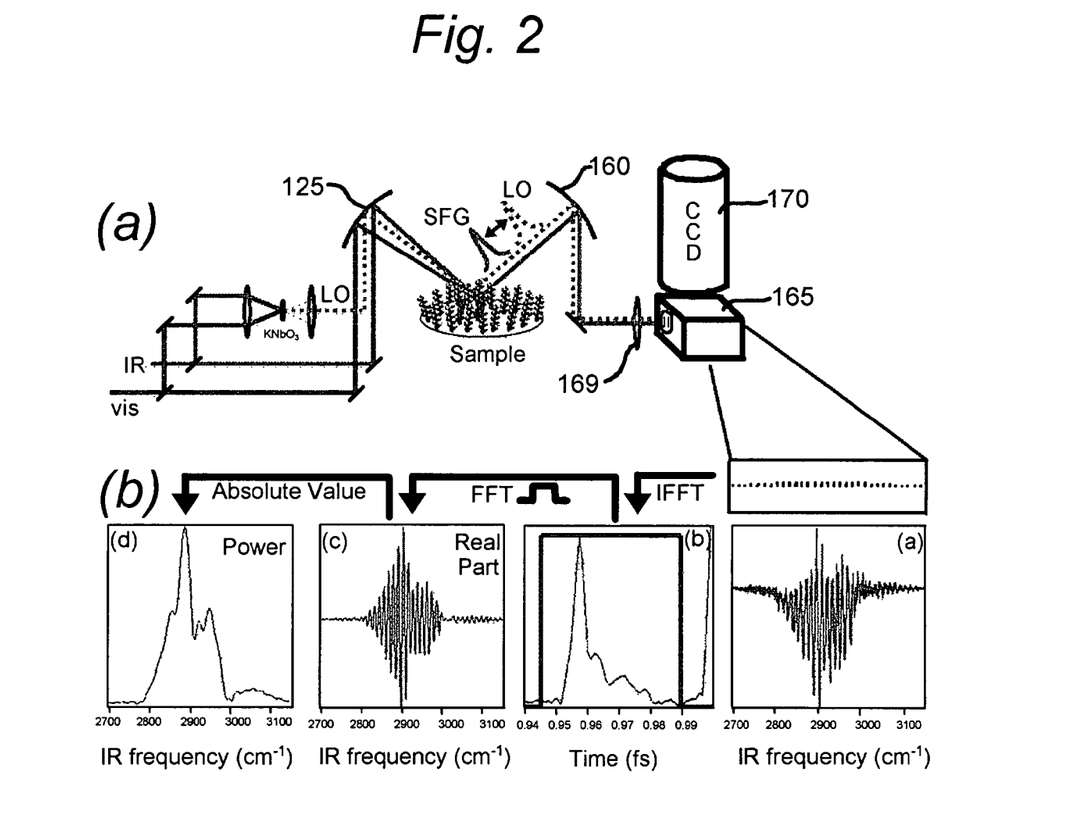
FIG. 2(a) is a simplified schematic representation of a spectroscopic apparatus constructed in accordance with the invention that is useful to describe the operation of the invention.
FIG. 2(b) is a sequence of graphical representations that illustrate the process of data analysis (a) raw interferogram obtained after subtraction of LO (b) time domain spectrum by inverse Fourier transformation.

FIG. 2(a) is a simplified schematic representation of a spectroscopic apparatus constructed in accordance with the invention that is useful to describe the operation of the invention, and FIG. 2(b) is a sequence of graphical representations that illustrate the process of data analysis beginning with graphical representation (a), which corresponds to a raw interferogram obtained after subtraction of LO, to graphical representation (b), which is a time domain spectrum derived by inverse Fourier transformation (IFFT). Elements of structure that have previously been discussed are similarly designated.

Graphical representation (c) of FIG. 2(b) illustrates the real part of the result of a FFT performed on the time domain spectrum of graphical representation (b). The absolute value of the real part shown in the frequency domain representation (c) is determined and shown in graphical representation (d) of FIG. 2(b).

In this embodiment, the local oscillator (LO) beam is generated by focusing ~1% of the visible and ~5% of the IR beams into a 1 mm thick $KNbO_3$ crystal. The intensity of LO beam is adjusted using a variable density filter (not shown). The desired delay between LO and the signal pulse is controlled by a manual delay stage (not shown in this figure). The LO beam is recombined with the visible beam, (parallel with a slight off-set), using a dichroic beam splitter. IR, visible, and LO beams are focused onto the sample surface in this specific illustrative embodiment of the invention by a 3" diameter, 45 cm-focal length on-axis parabolic mirror 125 to a ~230 μm diameter spot at the sample position. Before this mirror, the beams are parallel and vertically offset, such that they spatially overlap at the sample surface with the incidence angles ~65° and ~70° from the surface normal of the sample. The LO beam is aligned such that the reflected portion of the beam is collinear with the SFG signal produced at the sample surface. The SFG signal is collimated after the sample with a lens 169, focused onto an entrance slit (not specifically designated) of monochromator 165, then frequency-dispersed through the 300 mm monochromator (Acton Spectra-Pro 300i), and detected using a liquid nitrogen cooled CCD 170 (Princeton Instruments Spec-10:100B, 100×1340 pixels). SSP polarizations were used for the 1-octanol experiments. The spectra were recorded at the full resolution of CCD 170, i.e., 1340× 100 pixels, without binning, i.e., without combining the information in adjacent pixels.

A set of spectra was recorded for each sample. The LO spectrum (IR beam blocked) was measured, then HD signal was measured with visible, IR and LO opened. Additionally, the homodyne spectra (LO beam blocked) (and the corresponding background spectra with LO and IR are closed) was measured for samples with 1-octanol coverage concentrations 8% and above. The heterodyne spectrum (interference fringes) is then obtained by subtracting the measured LO signal from the measured HD signal. The homodyne spectrum is similarly obtained by subtracting the measured background spectrum from the measured homodyne spectrum. This procedure guarantees that the scattered light from the strong visible pump beam as well as CCD dark noise are subtracted for homodyne and heterodyne spectra.

At 100% 1-octanol monolayer coverage (1.0 mM bulk concentration), the total HD-SFG detected signal was ~22000 counts per pixel, the fringe depth of the spectral interferograms around the $CH_3$ symmetric stretch peak was 2400 counts, while the homodyne SFG signal level was ~200 counts per pixel for 100 second exposure time (no binning).

The heterodyne setup herein described was covered with a box (not shown) to eliminate the effects of air currents. The box cover increased the phase stability of the present arrangement to $\lambda/4$ over 10 minutes. In this manner, the fringe depth in the spectral interferograms was not affected by the phase drifts over 100 second long CCD collection times.

Experimental

The broad-band vibrational sum frequency generation (SFG) spectroscopy set-up test system, that has Octanol/Deuterated Octanol Mixture and an air/water interface, is based on a high power amplified femtosecond Ti-Sapphire laser system (Spectra Physics Spitfire sub-50 fs HP). One half of the 2 mJ fundamental output pulse (800 nm, FWHM 35 fs) is used to pump an Optical Parametric Amplifier (OPA) followed by the signal-idler re-timing with a manual delay stage and difference frequency mixing in a 0.5 mm thick $AgGaS_2$ crystal producing 4-5 µj IR pulses centered at 2900 cm$^{-1}$, temporal FWHM ~80 fs. The broad-band SFG scheme is employed that uses spectrally broad (FWHM~250 cm$^{-1}$) IR and narrow-band visible pulses (FWHM 15 cm$^{-1}$) obtained using a high-power deposited etalon (TecOptics). The laser power at the sample is 2-3 µJ/pulse for IR and up to $10^{-15}$ µJ/pulse for the visible at 1 kHz repetition rate. The SFG signal is collimated after the sample with a lens, focused onto a monochromator entrance slit, then frequency-dispersed through the 300 mm monochromator (Acton Spectra-Pro 300i), and detected using a liquid nitrogen cooled CCD (Princeton Instruments Spec-10:100B, 100×1340 pixels). SSP polarizations for SFG, visible, and IR beams, respectively, were used in all 1-octanol measurements.

Figure 3:
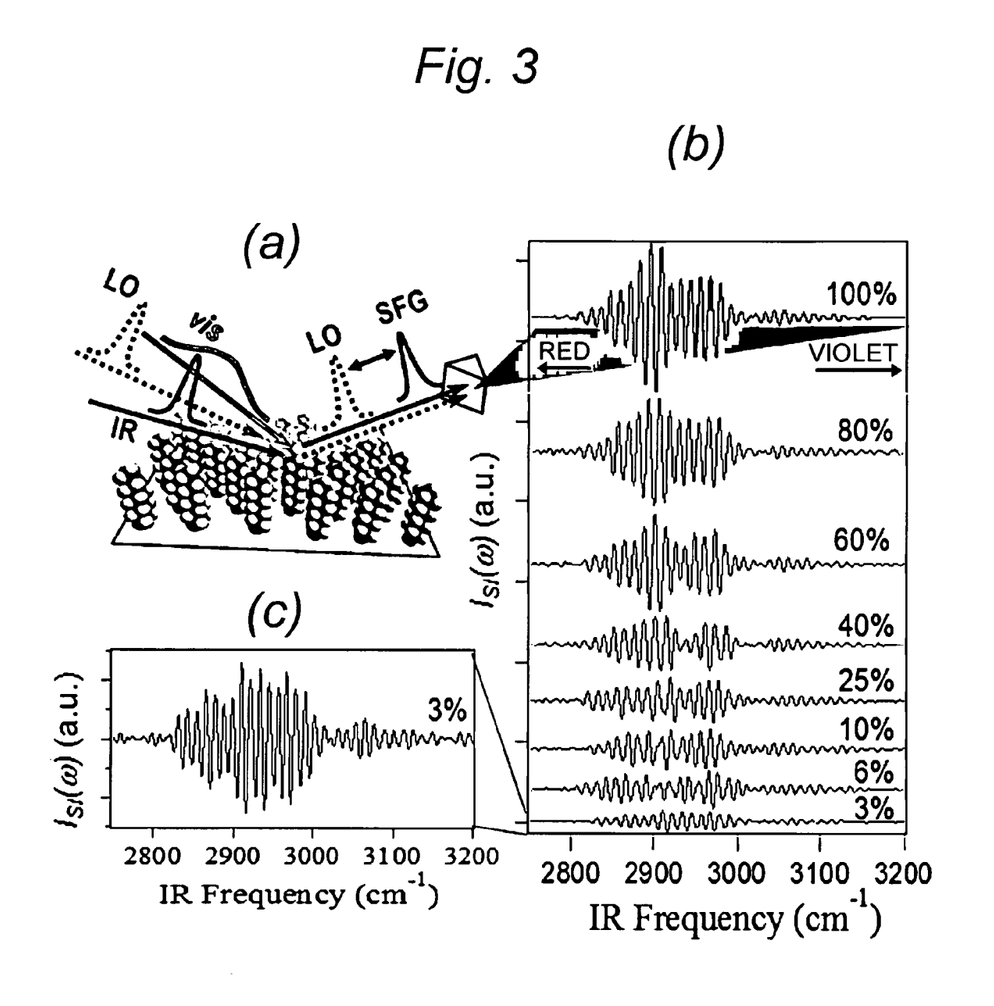
FIG. 3(a) is a schematic representation of the broad-band heterodyne-detected HD-SFG experiment.
FIG. 3(b) is a representation of Spectral Interferograms (SI, real part shown) for samples of varying surface coverage of 1-octanol, from 100% to 3% monolayer.
FIG. 3(c) is an expanded graphical representation of the signal from the 3% monolayer sample.

FIG. 3(a) is a schematic representation of the broad-band heterodyne-detected HD-SFG experiment; FIG. 3(b) is a representation of Spectral Interferograms (SI, real part shown) for samples of varying surface coverage of 1-octanol, from 100% to 3% monolayer; and FIG. 3(c) is an expanded graphical representation of the signal from the 3% monolayer sample. The reference LO beam in the HD-SFG set-up of FIGS. 3(a), 3(b), and 3(c) (hereinafter FIG. 3) is generated by sum-frequency mixing of small portions of the visible and IR beams (~1% of the visible and ~5% of the IR) in a 1 mm thick $KNbO_3$ crystal. The phase matching in the crystal has limited the spectral bandwidth of the LO to ~120 cm$^{-1}$ and its time width to ~250 fs. Intensity of LO beam is adjusted using a variable density filter to optimize detection of the cross-term. The LO beam is recombined with the visible beam using a dichroic beam splitter. IR, visible, and LO beams are spatially overlapped at the sample surface by a 3" diameter, 45 cm-focal length on-axis parabolic mirror focusing all beams into a ~230 µm diameter spot at the sample with 65° incidence angle from surface normal. The LO beam is aligned such that after reflection off the sample surface it propagates collinearly with the SFG signal generated at the sample surface (FIG. 3).

In this arrangement, $E_{SFG} \propto \chi^{(2)} \propto N$, and $I_{SFG} \propto |\chi^{(2)}|^2 \propto N^2$. Heterodyne detection is performed using spectral interferometry with a time-delayed (~2.5 ps, introduced by a manual delay stage) LO pulse, resulting in a characteristic fringe pattern $\propto e^{i\omega\tau}$ in the frequency domain referred to as spectral interferogram (FIG. 3). This allows one to utilize the broad-band SFG scheme and take advantage of multiplex detection with a CCD chip. Also, the fringe pattern is used to compensate for the phase drift between acquisitions using the phasing procedure as described below.

The spectral interferograms were recorded at the full resolution of the CCD (i.e., 1340 pixels) without binning. The overall HD signal level was adjusted by tuning the intensity of the LO beam, and is limited only by the dynamic range of the CCD detector (65535 counts/pixel). At 100% 1-octanol monolayer coverage (1.0 mM bulk concentration), the total HD-SFG detected signal (2) was typically ~22,000 counts per pixel, the fringe depth of the spectral interferograms (3) around the $CH_3$ symmetric stretch peak was 2,400 counts, while the homodyne SFG signal level (1) was ~200 counts per pixel for 100 second exposure time. The heterodyne setup is covered to eliminate the air currents, allowing the phase stability of $\lambda/4$ over 10 minutes. Thus the depth of the spectral fringes was not affected by the phase drifts over 100 second long CCD collection times used in all measurements.

It is demonstrated herein that the HD-SFG technique on a model system, mixed monolayers of 1-octanol/deuterated 1-octanol at the air/water interface. The samples were prepared using double-distilled water. 1-octanol ($C_8 11_{18}O$, Fisher Scientific, >99%) and deuterated 1-octanol ($C_8 13_{17}OH$, Cambridge Isotope Laboratories, 98%) were used as received. The overall concentration was kept constant at 1.0 mM, corresponding to a saturated Gibbs monolayer at the air/water interface, according to literature reports. A period of ten minutes was allowed for the monolayer to form at the surface before the SFG measurements. Evaporation, and the associated lowering of the sample surface, was controlled by covering the sample dish with a plastic film with two holes for beam access.

Results and Discussion

The $CH_3$ stretch modes in the 2800-3000 cm$^{-1}$ region were monitored while varying the mole fraction of 1-octanol, thus changing the surface coverage N of the $CH_3$ groups without the potential complications of changing molecular orientation and intermolecular packing of the alkane chains. For comparison, both heterodyne-detected and homodyne-detected SFG spectra obtained are presented using the same signal acquisition time on the CCD chip, 100 s. The two main transitions observed, marked by cyan shadows, are $CH_3$ symmetric stretch (~2880 cm$^{-1}$) and Fermi resonance (2940 cm$^{-1}$), in agreement with the previously reported measurements for SSP polarization.

The broad-band HD-SFG spectral interferograms are obtained by recording the total heterodyne-detected intensity spectrum $I_{D.-SFG}$, Eq. (2), then subtracting the LO intensity spectrum (second term in Eq. (2)) to reveal the cross-term, Eq. (3). The LO intensity spectrum is recorded on the same CCD detector, in exactly the same experimental configuration, by simply blocking the IR beam such that the SFG signal from sample is not generated. After subtraction of the LO, an inverse Fourier transform into the time-domain is performed to filter out the remaining homodyne contribution centered at $\tau=0$ delay (center of LO pulse), since the desired cross-term, Eq. (3), is centered around $\tau=2.5$ ps delay between the LO and SFG pulses. Fourier transforming back into the frequency domain yields the "cleaned-up" spectral interferogram (SI) shown in FIG. 3(b) (real part shown), with the LO spectral envelope completely removed. Clean spectral interferograms can be recorded using the 100 s CCD acquisition time for samples ranging from 100% 1-octanol in the monolayer to a fully deuterated monolayer, the signal of which is referred to below as the background signal of the neat interface. FIG. 3(c) shows a blow-up of the spectral interferogram for the 3%

1-octanol monolayer sample, demonstrating the signal-to-noise level achievable in this technique. In fact, interferograms for samples below 1% octanol monolayer can be recorded with similar S/N, but the analysis of the spectra is restricted due to the purity of the d-octanol.

Figure 4:
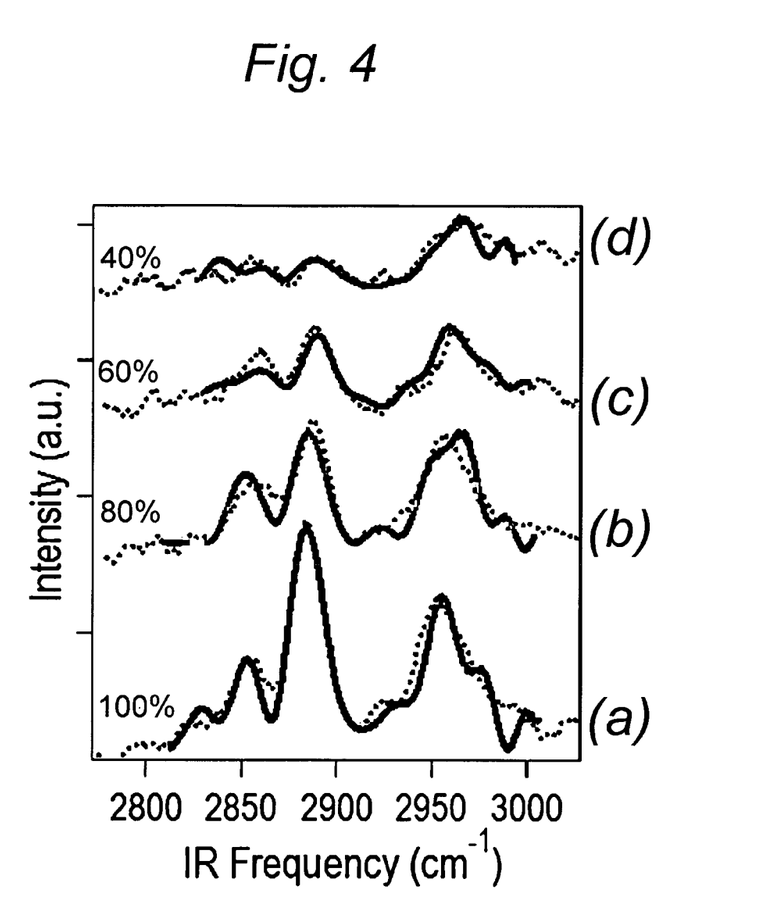
FIG. 4 is a graphical representation of the comparison of the power spectra of 1-octanol CH-stretch vibrations obtained from the heterodyne-detected spectral interferograms (thick colored lines) with the conventional (homodyne-detected) SFG spectra (black dashed lines) for surface coverage (A) 100%, (B) 80%, (C) 60%, and (D) 40% monolayer.
Figure 6:
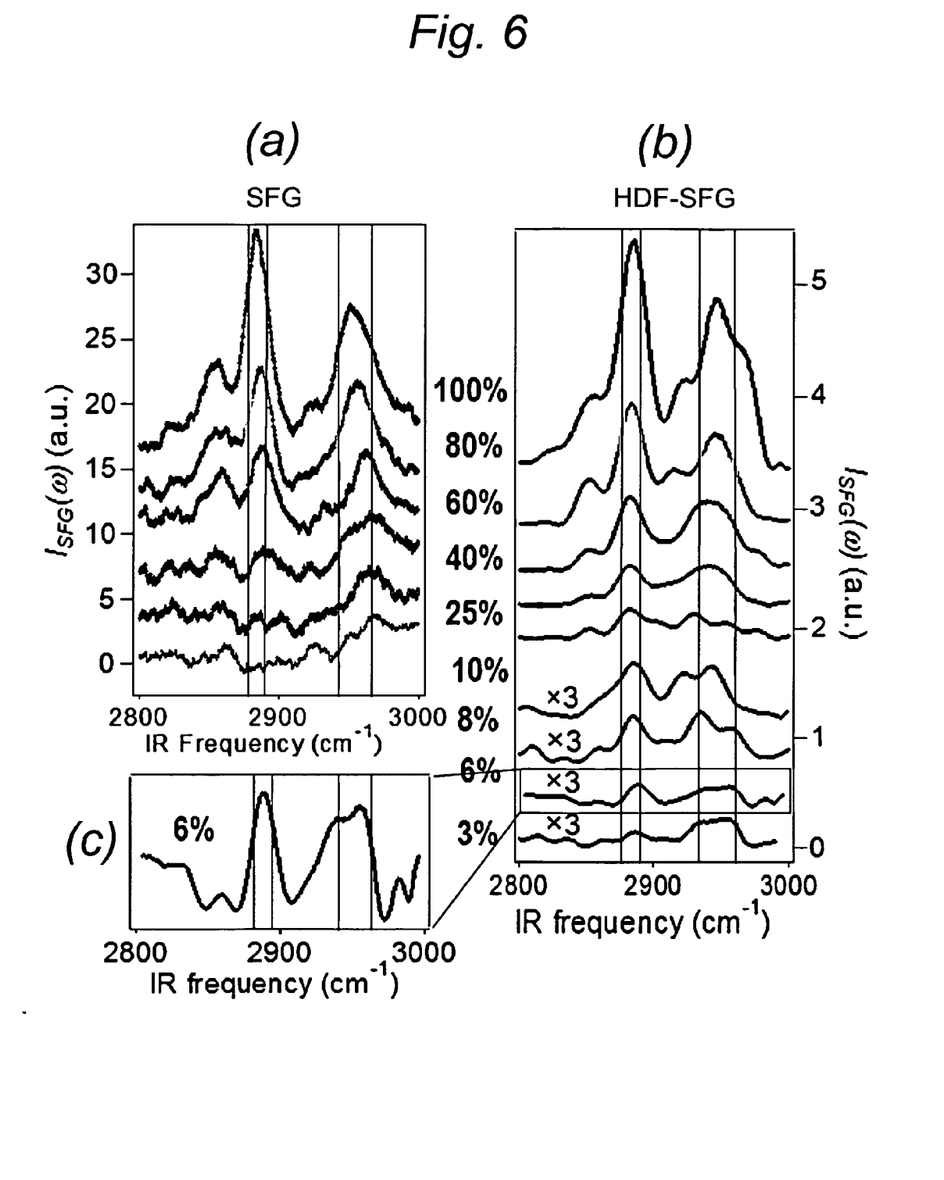
FIG. 6(a) is a graphical representation of the homodyne-detected SFG spectra of CH-stretch of saturated octanol/d-octanol monolayers (octanol mole fraction indicated) at different surface coverage obtained using 100 s acquisition time.
FIG. 6(b) is a graphical representation of the heterodyne-detected power spectra extracted from the spectral interferograms after subtracting out the background signal from neat interface, 100 s acquisition time.
FIG. 6(c) is an expanded graphical representation of the heterodyne-detected spectrum of the 6% monolayer.

FIG. 4 is a graphical representation of the comparison of the power spectra of 1-octanol CH-stretch vibrations obtained from the heterodyne-detected spectral interferograms (solid lines) with the conventional (homodyne-detected) SFG spectra (dotted lines) for surface coverage (a) 100%, (b) 80%, (c) 60%, and (d) 40% monolayer. Absolute value squared of the obtained interferograms, corrected for the spectrum of the local oscillator, accurately reproduce the homodyne-detected SFG spectra as shown in FIG. 4, thereby validating the HD-SFG measurements. However, the comparison can be made only for samples close to monolayer coverage. Below ~40% monolayer, the homodyne-detected SFG does not produce useful spectra for the chosen 100 s acquisition time. The two main reasons for this are (1) that the resonant part of the homodyne SFG signal decreases quadratically with the surface coverage N (see, Eq. (1)), quickly reducing the resonant octanol signal below the noise level, and (2) that at low coverage, the background part of the response (nonresonant electronic contribution as well as impurities and the broad red-tail of the water OH-stretch band evident in FIG. 6(a) interferes with and masks the weak resonant CH-stretch transitions.

Heterodyne detection overcomes both of these problems. First, the use of the strong LO beam amplifies the overall signal, improving the signal-to-noise ratio. Second, the knowledge of the absolute phase of the HD-SFG signal with respect to the background signal from neat interface (100% deuterated 1-octanol monolayer) enables correct subtraction of the background contribution to reveal the resonant 1-octanol signal.

The value of the absolute phase cannot be preserved from experiment to experiment, due to long-term drift and especially when samples are changed. In order to lock the phases in all measurements, the following phasing procedure has been developed. Neat interfaces (in the present case, 100% deuterated 1-octanol monolayer at the air/water interface) are often characterized by predominantly non-resonant response leading to a broad SFG signal spectrum. The region around 3100 cm$^{-1}$ is outside the CH$_3$ vibrational transitions of interest. The neat interface SFG background is nonzero in this region (FIG. 3(b)), resulting possibly from the broad red-tail of the water OH-stretch band. SFG signal in this region does not depend on the 1-octanol surface coverage ranging from 0% to 100%.

Figure 5:
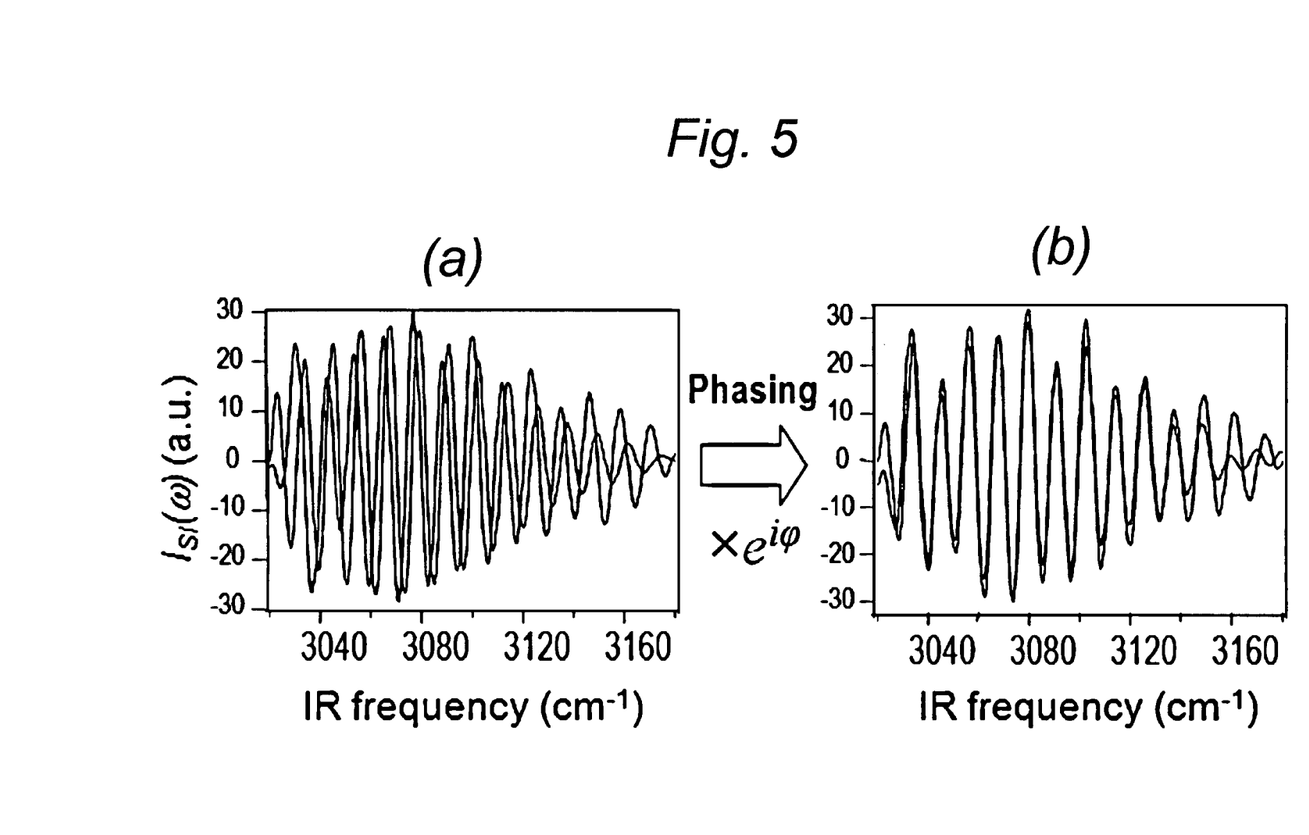
FIG. 5(a) is a graphical representation of a phasing procedure allowing to lock the phase of the spectral interferograms (SI) to that of the background signal of neat (fully deuterated) interface.
FIG. 5(b) is a graphical representation of the real parts of the SI from 10% octanol monolayer sample and neat interface before phasing in the spectral region around 3100 cm$^{-1}$, corresponding to the same two SI after phasing (interferogram multiplied by $e^{i\omega_{adj}}$)

FIG. 5(a) shows magnified HD-SFG spectral interferograms at approximately 3100 cm$^{-1}$ for the neat interface (N=0%) and for a sample with N=10% 1-octanol interface coverage. The shapes of the spectral interferograms for both concentrations are similar in this spectral region, but the phases differ. By adding a phase $\phi_{adj}$ to the complex-valued HD-SFG spectral interferogram for the 10% sample (i.e., multiplying it by a $e^{i\phi_{adj}}$ factor), one can achieve nearly perfect overlap in this spectral region (FIG. 5(b)), thus locking the phase of the 10% sample to the 0% (neat interface) sample (background). The accuracy of the obtained phase $\phi_{adj}$ is better than ±5 degrees. Using this phasing procedure, one ensures that the absolute phases for all measured samples are locked to the spectral phase of the 0% reference sample (100% deuterated 1-octanol). The ability to retrieve absolute phase for each measured spectrum (with respect to a chosen "standard" zero-phase signal, e.g., neat interface background) using simple phasing of the spectral interferograms is a consequence of the phase being locked across the spectrum of the LO pulse, a unique advantage of the broad-band spectral interferometry approach not available, e.g., in the scanning phase-sensitive SFG detection.

After the phasing procedure, the background signal of the neat interface (100% deuterated 1-octanol) can be subtracted to reveal the spectral signatures of the analyte (1-octanol) which are otherwise masked, especially at low concentrations. The extracted background-free HD-SFG power spectra shown in FIG. 6(b) demonstrate that this technique enables vibrational spectroscopy of surfaces at coverage as low as a few % monolayer, greatly exceeding the sensitivity limits of conventional SFG spectroscopy (FIG. 6(a)). As an example, the HD-SFG spectrum for the 6% monolayer sample (FIG. 6(c)) exhibits the same two main transitions, i.e., the CH$_3$ symmetric stretch and Fermi resonance, as in the higher concentration samples. The increased noise level on the wings of the spectrum results from the limited bandwidth of the LO pulse in the current set-up (only ~120 cm$^{-1}$ due to phase-matching in the KNbO$_3$ crystal).

Figure 7:
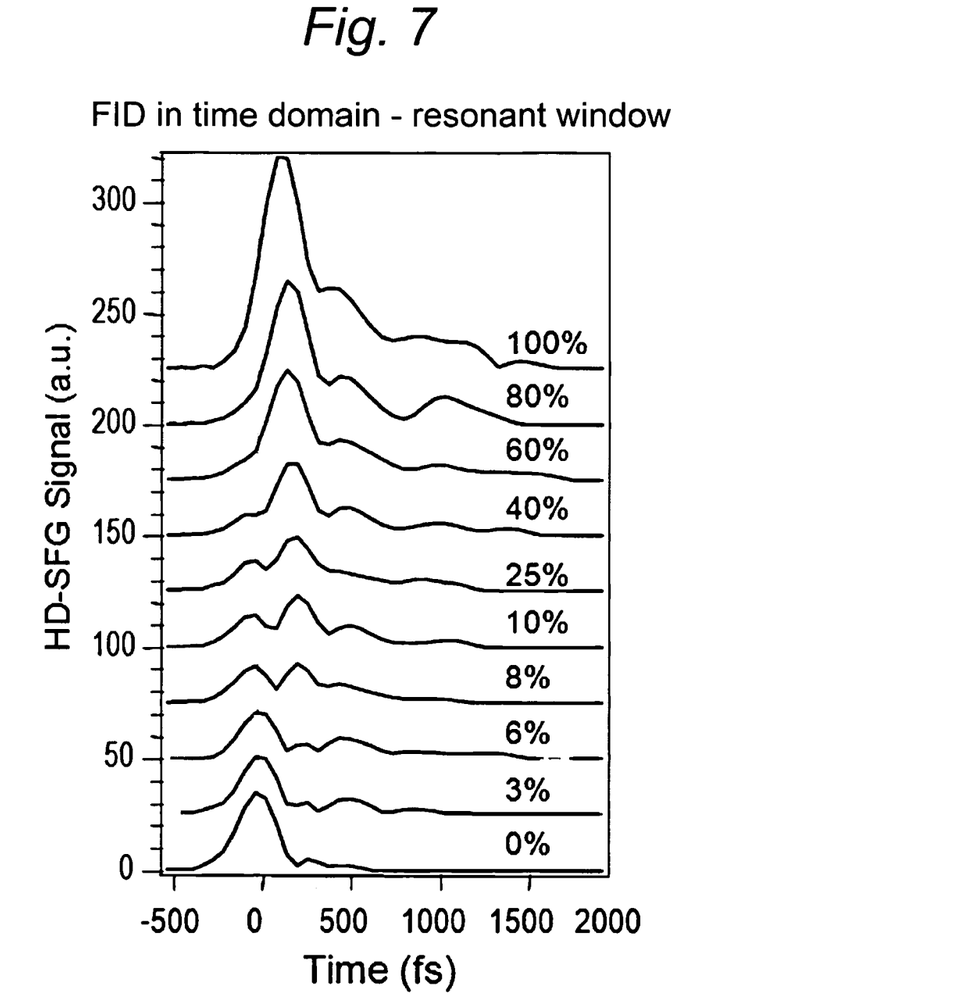
FIG. 7 is a graphical representation of the Time-domain Free Induction Decays signals at various 1-octanol mole fractions in the monolayer, showing vibrational quantum beats of the CH-stretches of 1-octanol and the background response of the neat (0%, fully deuterated) interface consisting of both nonresonant component peaked at t+0 and resonant vibrations of impurities (≦2% manufacturer specifications).

The time-domain representation (FIG. 7) naturally separates out the mostly nonresonant (i.e., instantaneous) background signal from the resonant part of the response—the Free Induction Decay (FID) which shows the characteristic vibrational quantum beats. The neat interface background signal (FIG. 7, bottom trace) was measured by performing HD-SFG on a fully deuterated monolayer. The clearly discernible non-instantaneous component in the time-dependent signal from the neat interface sample demonstrates our ability to detect impurities in the deuterated 1-octanol (2% or below, according to the manufacturer). It is to be noted that the knowledge of the absolute phase allows one to subtract this neat interface signal, i.e., essentially get rid of the impurities contaminating the 1-octanol spectrum at low concentrations. For intermediate concentrations (8-25%), the FID curves show destructive interference between the background FED signal peaked around t=0 and the resonant octanol signal, resulting in an apparent "dip" in the overall HD.

Figure 8:
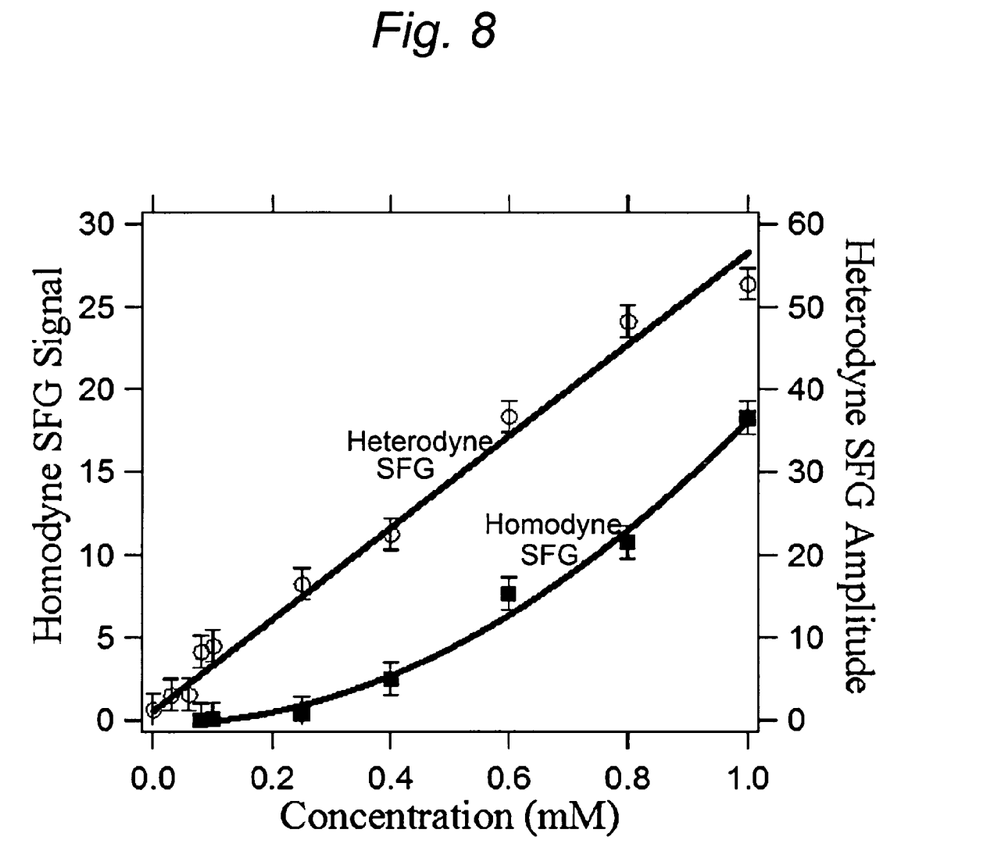
FIG. 8 is a graphical representation of the scaling of the homodyne-detected SFG intensity (squares) and HD-SFG signal amplitude (circles) with the surface coverage (1-octanol mole fraction in the monolayer) for the $CH_3$ symmetric stretch mode.

The linear scaling of the resonant (background-free) CH-stretch HD-SFG signal with the octanol mole fraction is demonstrated in FIG. 8 which shows peak amplitude of the CH$_3$ symmetric stretch resonance. This allows extension of the HD-SFG spectroscopy to samples with surface coverage significantly below a single monolayer. In addition, the signal amplitude is much larger for the HD-SFG, which alleviates the problem of the electronic read-out noise. On the contrary, the homodyne-detected SFG intensity of the same transition follows the expected quadratic scaling. Note that homodyne SFG signal is zero within the S/N for surface coverages 25% monolayer and below.

The signal-to-noise ratio in the spectral interferograms and the extracted spectra (FIGS. 3 and 6) for lower coverage samples permits the suggestion that HD-SFG will enable the obtaining of vibrational spectra for samples at or below 1% monolayer coverage. In fact, several spectral interferograms were recorded for the 1-octanol mole fraction of 1%, 0.5% and 0.1% (not shown), with S/N similar to that in FIG. 3. However, the isotopic purity of the deuterated 1-octanol provided by the supplier (Cambridge Isotope Laboratories) is 98%. Thus, for the chosen model system, testing of the HD-SFG technique at low surface coverages is limited by the chemical purity of the samples rather than by the sensitivity of the spectroscopic detection.

Heterodyne detection via broad-band spectral interferometry has herein been implemented in accordance with the invention, yielding several significant advantages. First, the reference beam does not have to be scanned across the SFG signal and the whole spectral phase and amplitude can be detected from one CCD reading. This eliminates phase fluctuations that result from wavelength tuning. Second, the FFT procedures used herein enable the implementation of significant noise filtering. Third, the instrument of the present invention is possessed of a phase stability that is long enough to retrieve one SFG spectrum without phase drift-off, thereby enabling retrieval of the SFG spectrum. In addition, the inventive phasing procedure allows the LO phase between different measurements to be locked, thereby solving the problem of phase stability. The recovered spectral phase contains information on absolute molecular orientations and enables recovery of the temporal SFG signal profile, which contains information on molecular dynamics at interfaces.

Theory of Operation

The interface SFG signal results from the second order nonlinear process of two electric fields interacting with the surface/interface. The spectral component of the SFG signal electric field at frequency $\omega$ is given by:

$$E_{SFG}(\omega) \propto \iint x^{(2)}(\omega=\omega_{IR}+\omega_{VIS},\omega_{IR},\omega_{VIS}) E_{IR}(\omega_{IR}) E_{VIS}(\omega_{VIS}) d\omega_{VIS} d\omega_{IR}, \quad (A)$$

$$x^{(2)} = N \langle \beta^{(2)} \rangle \quad (B)$$

Here $E_{VIS}$ and $E_{IR}$ are spectral components of the visible and IR laser beams at frequencies $\omega_{VIS}$ and $\omega_{IR}$ respectively. $x^{(2)}$ is the second order nonlinear susceptibility tensor proportional to the monolayer coverage N and to the averaged molecular polarizability tensor $\langle \beta^{(2)} \rangle$.

SFG is implemented with spectrally narrow nonresonant visible laser pulse and spectrally broad IR pulse resonant with the adsorbant so that equation (A) becomes $$E_{SFG}(\omega) \propto N \cdot E_{VIS} \cdot \int \langle \beta^{(2)}(\omega=\omega_{IR}+\omega_{VIS},\omega_{IR},\omega_{VIS}) \rangle \cdot E_{IR}(\omega_{IR}) d\omega_{IR} = N \cdot E_{VIS} \cdot \langle \beta^{(2)} \rangle \quad (C)$$

$$I_{SFG}^{homo}(\omega) = |\hat{E}_{SFG}(\omega)|^2 \propto N^2 \cdot |\langle \tilde{\beta} \rangle|^2$$

The integral in equation (C), denoted as $\langle \beta^{(2)} \rangle$, contains the spectral overlap of the IR laser pulse with the average molecular polarizability $\langle \beta^{(2)} \rangle$.

The homodyne-detected signal:

$$S_{SFG}^{homo}(\omega) \propto N^2 |\langle \beta \rangle|^2 \quad (D)$$

depends quadratically on the monolayer coverage N. This quadratic dependence strongly limits the sensitivity of the homodyne detection technique at low adsorbant coverage. For instance, if the coverage is reduced by a factor of 10, the signal to noise ratio would reduce by 100, and the experimental exposure would time need to be increased by $10^4$ to keep the same signal-to-noise ratio.

In the heterodyne detection two collinear beams, a LO beam is made to propagate collinearly with the SFG signal generated at the sample surface, such that they interfere at the detector. The heterodyne detected signal intensity is:

$$S_{SFG}^{hd}(\omega) \propto |\hat{E}_{SFG}(\omega) + \hat{E}^{LO}(\omega)|^2 = |\hat{E}_{SFG}(\omega)|^2 + |\hat{E}_{LO}(\omega)|^2 + S_{SFG}^{hd-cross-term}(\omega), \quad (E)$$

$$S_{SFG}^{hd-cross-term}(\omega) = 2|\hat{E}_{SFG}(\omega)\hat{E}_{LO}(\omega)|\cos(\phi_{SFG}(\omega)-\phi_{LO}(\omega)) \propto N \cdot |\langle \tilde{\beta}^{(2)} \rangle| \quad (F)$$

$|\hat{E}_{SFG}(\omega)|^2$ and $|\hat{E}_{LO}(\omega)|^2$ are spectral intensities of SFG and LO. The cross-term $$I_{SFG}^{hd-cross-term}$$

contains the product of the two fields and depends on the signal phase. In heterodyne detection the cross term is extracted by separately measuring the heterodyne intensity (E) and the intensity of the Local Oscillator (second term in (E)), then subtracting one from the other. Note that the homodyne intensity of the SFG signal $$|\hat{E}_{SFG}(\omega)|^2$$

is small compared to that of the LO. The cross-term (F) is relatively increased by using intense LO beam and its phase can be measured. The cross term scales linearly with the surface coverage N. Thus if the coverage drops by a factor of 10, as in previous example, its value also drops 10 times and the exposure would have to be increased 100 times to keep the same signal to noise ratio, i.e., 100 times shorter than in the homodyne detection case.

If the LO pulse is temporarily delayed with respect to the SFG signal pulse by a delay $\tau_0$, it acquires an additional phase $\omega\tau_0$, and the cross term exhibits fast oscillations as a function of frequency, due to the $\phi_{SFG}(\omega)-\phi_{LO}(\omega)-\omega\tau_0$ phase in the cosine term, with period $2\pi/\tau_0$—the so-called "spectral interferogram." By applying spectral interferometry (SI) procedure, both the signal spectral phase and its amplitude can be recovered. Moreover, the temporal profile of the signal (FID) can be recovered through the Fourier transform.

Finally, most interfaces produce nonresonant SFG background signal even when the adsorbant molecule of interest is not present. This background signal $E_{BGR}$ interferes with the adsorbant signal and strongly limits the sensitivity of the homodyne detection. Indeed, the total measured homodyne signal intensity is:

$$|\hat{E}_{SFG}(\omega)+\hat{E}_{BGR}(\omega)|^2 = \hat{E}_{SFG}^2(\omega)+\hat{E}_{BGR}^2(\omega)+2|\hat{E}_{SFG}(\omega)\hat{E}_{BGR}(\omega)|\cos(\phi_{SFG}(\omega)-\phi_{BGR}(\omega)) \quad (G)$$

where $E_{SFG}$ and $E_{BGR}$ are SFG signals from the adsorbant of interest and the neat interface respectively. The phase $\phi_{SFG}(\omega)-\phi_{BGR}(\omega)$ is not recoverable in the homodyne experiments. At relatively low adsorbant signal levels, some of its spectral features in the measured homodyne signal may be amplified, while others suppressed due to the interference. Heterodyne detection recovers the signal phase, and thus allows subtraction of the separately measured nonresonant interface signal $E_{BGR}$. This enable extraction of adsorbant signals at levels well below the neat interface SFG background value.

Although the invention has been described in terms of specific embodiments and applications, persons skilled in the art may, in light of this teaching, generate additional embodiments without exceeding the scope or departing from the spirit of the invention described and claimed herein. Accordingly, it is to be understood that the drawing and description in this disclosure are proffered to facilitate comprehension of the invention, and should not be construed to limit the scope thereof.

What is claimed is:

1. A method of performing spectroscopy, the method comprising the steps of:
   combining in an optical circuit first portions of first and second input light beams to form a reference beam;
   focusing second portions of the first and second light beams and the reference beam onto a sample desired to be investigated;
   receiving a reflected light beam from the sample at an input of a monochromator; and
   viewing a predetermined wavelength band of the reflected light beam at an output of the monochromator.

2. The method of claim 1 wherein said step of combining comprises the step of propagating the first portions of the first light beam and the second light beam through a crystal.

3. The method of claim 2, wherein said step of propagating the first portions of the first light beam and the second light beam through a crystal comprises the further step of difference frequency mixing.

4. The method of claim 2, wherein the first light beam is an IR light, the second light beam is a visible light, and the crystal is formed of $KNbO_3$.

5. The method of claim 1, wherein said step of viewing comprises the further step of propagating the predetermined wavelength band of the reflected light beam from the output of the monochromator to a camera.

6. The method of claim 1, wherein there is further provided the step of subjecting the predetermined wavelength band of the reflected light beam to inverse Fourier transformation to produce a corresponding time-domain representation of the predetermined wavelength band of the reflected light beam.

7. The method of claim 6, the time-domain representation of the predetermined wavelength band of the reflected light beam is subjected to the step of fast Fourier transform (FFT) and the real part of the resulting frequency domain representation is extracted.

8. The method of claim 7, wherein there is further provided the step of determining an absolute value of the real part of the resulting frequency domain representation.

9. The method of claim 1, wherein there is further provided the step of interposing an optical delay stage in the path of a selected one of the first and second light beams.

10. A spectroscopy system comprising:
   an optical circuit having first and second inputs for receiving respective ones of first and second beams of electromagnetic energy;
   a beam splitter for splitting the first beam of electromagnetic energy into first and second sub-beams of electromagnetic energy;
   a crystal for propagating the first sub-beam of electromagnetic energy of the first beam of electromagnetic energy and the second beam of electromagnetic energy simultaneously, to produce a combined reference beam of electromagnetic energy; and
   a reflector element for directing the reference beam toward a sample that is desired to be investigated.

11. The spectroscopy system of claim 10, wherein there is further provided a monochromator for receiving a reflection of the reference beam from the sample.

12. The spectroscopy system of claim 11, wherein there is further provided an analysis system for conducting a Fourier transformation on the output of said monochromator.

13. The spectroscopy system of claim 10, wherein said reflector element additionally direct the second beam of electromagnetic energy and the second sub-beam of electromagnetic energy of the first beam of electromagnetic energy toward the sample that is desired to be investigated.

14. The spectroscopy system of claim 10, wherein said crystal is a $AgGaS_2$ crystal.

15. The spectroscopy system of claim 10, wherein said crystal is a $KNbO_3$ crystal.

16. The spectroscopy system of claim 10, wherein there is further provided an optical delay stage in the propagation path of the first beam.

17. A method of performing spectroscopy, the method comprising the steps of:
   splitting each of first and second beams of electromagnetic energy to form respectively associated first and second component beams for each of the first and second beams of electromagnetic energy;
   combining the first component beams of each of the first and second light beams in a crystal to form a reference beam; and
   focusing the reference beam onto a sample desired to be investigated.

18. The method of claim 17, wherein said step of focusing the reference beam onto a sample desired to be investigated comprises the further step of focusing the second component beams of each of the first and second light beams onto the sample desired to be investigated.

19. The method of claim 18, wherein there is further provided the step of receiving electromagnetic energy reflected from the sample at an input of a monochromator.

20. The method of claim 19, wherein prior to performing said step of receiving electromagnetic energy reflected from the sample at an input of a monochromator there is provided the further step of collimating the electromagnetic energy reflected from the sample.

* * * * *